US006910394B2

(12) United States Patent
Kriel

(10) Patent No.: US 6,910,394 B2
(45) Date of Patent: Jun. 28, 2005

(54) CHROMATOGRAPH VALVE AND METHOD OF USE

(76) Inventor: Wayne A. Kriel, 506 Lakeside, Friendswood, TX (US) 77546

(\*) Notice: Subject to any disclaimer, the term of this patent is extended or adjusted under 35 U.S.C. 154(b) by 187 days.

(21) Appl. No.: 10/160,973

(22) Filed: May 30, 2002

(65) Prior Publication Data

US 2002/0178843 A1 Dec. 5, 2002

Related U.S. Application Data

(60) Provisional application No. 60/294,725, filed on May 31, 2001.

(51) Int. Cl.$^7$ ................................................. G01N 1/00
(52) U.S. Cl. ................................................. 73/863.11
(58) Field of Search ............................ 73/23.41, 23.42, 73/863.73, 863.11, 864.83, 864.84; 422/103

(56) References Cited

U.S. PATENT DOCUMENTS

| | | | | |
|---|---|---|---|---|
| 2,830,738 A | \* | 4/1958 | Sorg et al. ............... | 73/863.73 |
| 3,559,703 A | \* | 2/1971 | Maul et al. ................ | 141/329 |
| 3,681,998 A | \* | 8/1972 | Karas et al. ............. | 73/863.73 |
| 3,733,908 A | \* | 5/1973 | Linenberg ................ | 73/863.12 |
| 3,889,538 A | \* | 6/1975 | Fingerle ................... | 73/863.11 |
| 4,429,584 A | \* | 2/1984 | Beyer et al. ............. | 73/864.21 |
| 4,576,917 A | \* | 3/1986 | Schabron .................. | 436/85 |
| 5,089,234 A | \* | 2/1992 | Preston .................... | 422/103 |

OTHER PUBLICATIONS

Website printout—VICI Sampling and Switching Valves (medium) (2 pages) © 1999.
Website printout—VICI Sampling and Switching Valves (high) (2 pages) © 1999.
Website printout—Valco Multiposition Valves (2 pages) © 1999.
Website printout—VICI Injectors anfd Switching Valves, Nov. 2002.
Website printout—VICI Microvolume Sample Injection© 1999.
Website printout—VICI—Microvolume Sample Injections, Nov. 2002.
Website printout—Valco Valves (from catalog) (2 pages) No Date.

\* cited by examiner

*Primary Examiner*—Robert Raevis
(74) *Attorney, Agent, or Firm*—Rankin, Hill, Porter & Clark LLP

(57) ABSTRACT

An improved chromatograph valve is provided which may be placed in close proximity to a chromatograph in order to avoid temperature variations in the space therebetween. The valve may include a multiple sample slot rotor movable in a single direction to reduce wear upon the rotor and valve body. The rotor sample slots as well as the pairs of sample and carrier gas ports upon the valve body may be diametrically opposed to allow a superior temperature gradient to be created across the valve, the gradient allowing a sample material to enter the valve in a single phase and exit the valve sufficiently volatilized.

6 Claims, 4 Drawing Sheets

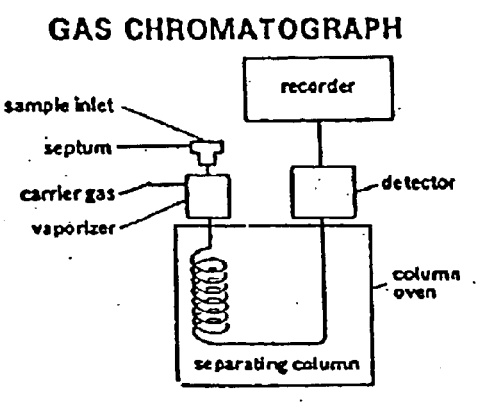
Figure 1 - PRIOR ART
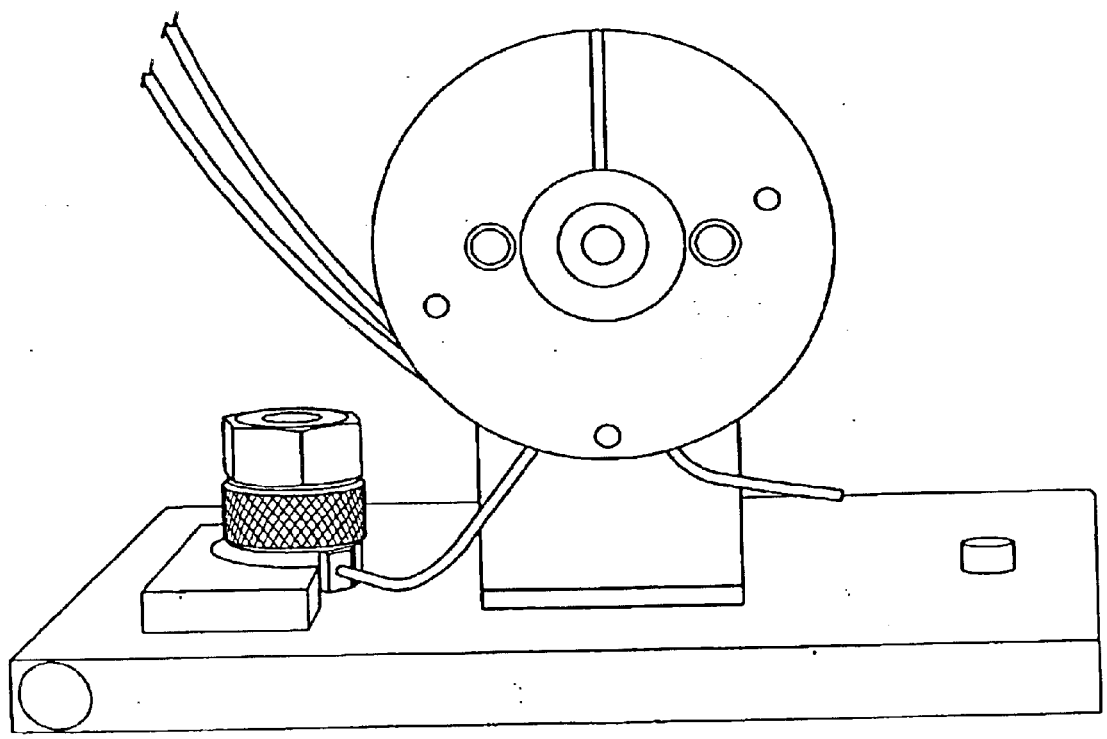
Figure 2
(PRIOR ART)

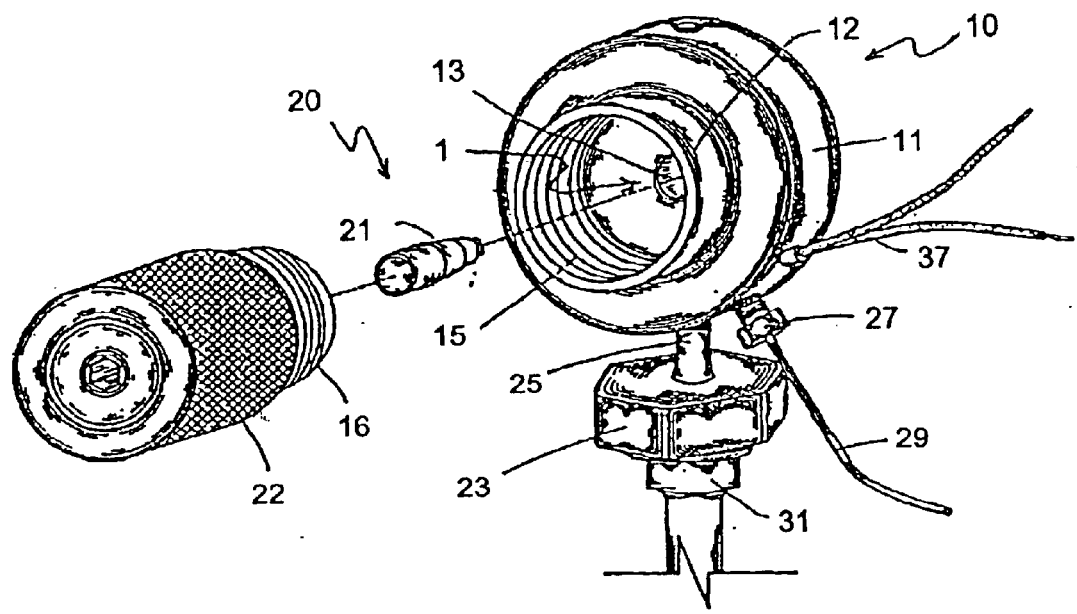
Figure 3
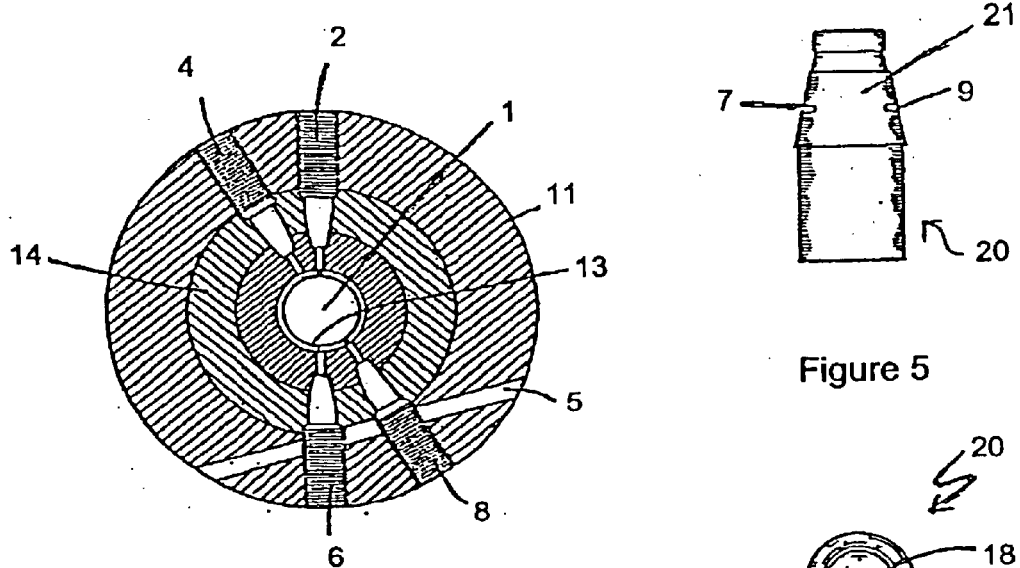
Figure 4
Figure 5
Figure 6

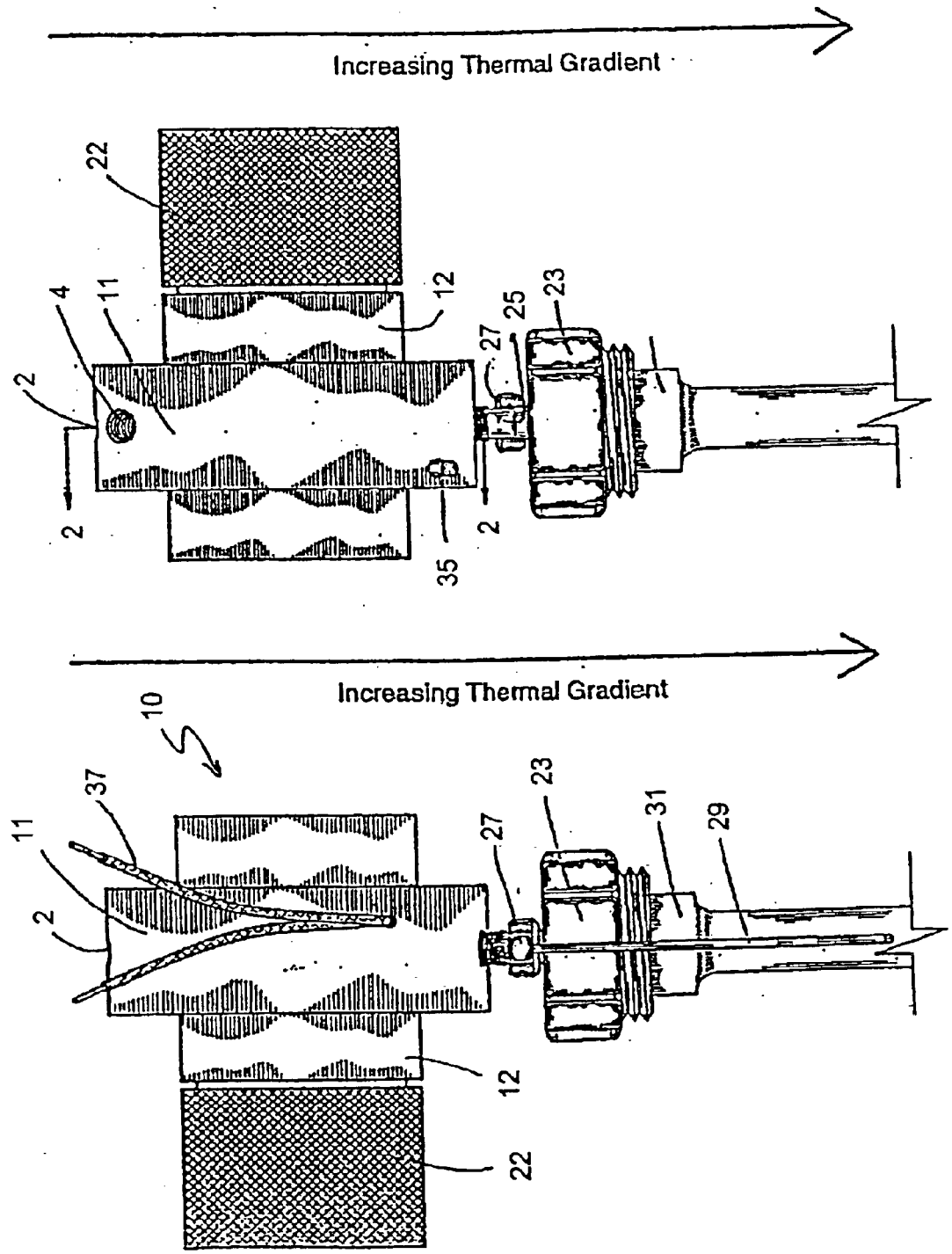

CHROMATOGRAPH VALVE AND METHOD OF USE

PRIORITY CLAIM

This application claims the benefit of U.S. provisional patent application No. 60/294,725 filed on May 31, 2001 the entirety of which is hereby incorporated by reference.

FIELD OF INVENTION

The present invention relates to a valve adapted for use with a chromatograph, specifically, to a valve providing direct entry to the chromatograph without auxiliary prevolatilization heating or post-injection cooling of the sample.

BACKGROUND OF THE INVENTION

In the field of chemical analysis, the gas chromatograph (GC) has been a mainstay of chemists since the early 1950's. The basic gas chromatograph as shown in FIG. 1 includes four functional units: an inlet for sample material, a carrier gas supply, a separating column, and a detector for sensing the composition of the column effluent. A measured sample is introduced through the sample inlet and vaporized within the carrier gas prior to entry into the separating column. The sample inlet may include a septum or other structural components. The material to be sampled may be introduced via a syringe or other means. A variation of the gas chromatograph involves using a precision valve, shown in FIG. 2, to obtain the measured amount of sample material, initially in a liquid form, for testing within the chromatograph. The supply of carrier gas is routed into the valve to sweep the measured sample from the valve to an interior side of a septum (if used) upon the chromatograph, and then into the column. No matter what type of measuring technique or structure of the sample inlet is used, a liquid sample must be adequately vaporized before entering the separating column unit of the chromatograph.

In the chromatograph variation using a precision valve, the sample may be vaporized within the valve prior to entry of the sample inlet. The accuracy of sample size and the control of the sample temperature (control of vaporization) are both critical to accurate analysis. Detector readings are evaluated in combination with sample size to determine the concentration of materials within sample material. Non uniform sample size directly affects final concentration calculations. Wear within the valve body can affect the precision machined slots and passages in the valve which carry the measured sample, thus, affecting the uniformity of sample size.

Temperature control is critical to the successful analysis of the sample material in any GC apparatus. Temperature of the sample material at the inlet of the precision valve must be kept low enough to prevent pre-volatilization of the sample material. The volume of a partially volatilized sample varies from a non-volatilized sample, thus, pre-volatilization creates non-uniform sample sizes. Temperature at the outlet of the valve and between the valve and sample inlet must be maintained within a desired range in order to prevent inadvertent condensation of the sample after it has been volatilized. Condensation can prevent the separating column from functioning correctly for the sample material being analyzed and condensed material may remain in the column, sample inlet and/or transfer lines rendering future measurements inaccurate as well.

Numerous devices are marketed to provide valve arrangements for chromatographic devices. Sampling valves are generally either rotary valves or push-pull valves. Those marketed by Valco Instruments Co., Inc. of Houston, Tex., are representative of the types of valves currently available in the market. Insulated heater valve enclosures are combined with the valve and sometimes the sample inlet to control the temperature of the valve and sample independently of the column temperature. These heated valve enclosures are ovens, which are placed over the body of the valve or sample inlet and connected to a source of current to heat the elements within the oven. Sensors must be employed on these independent heater elements to monitor and adjust the temperature of the valve body to avoid overheating the valve body with the sample enclosed. FIG. 2 shows a known cylindrical heater element inserted within a sleeve which is wrapped around the valve body.

In each of the existing valves, despite the separate heater elements, there are opportunities for the sample to cool in transit from the valve body to the column of the GC especially when the heater elements are adjusted to avoid pre-volatilization conditions. A typical point of condensation is within tubing which runs from the valve to the sample inlet. What is desired is a valve which avoids undue wear and which can repeatedly and accurately capture a measured sample from an inlet stream of sample material, manipulate and maintain the temperature of the sample as desired, and deliver a vaporized sample to the sample inlet and separating column of a chromatograph.

SUMMARY OF THE INVENTION

A chromatograph valve is provided for capturing sample material, the valve including a valve body with a first pair of ports formed through an exterior portion of the body. The first pair of ports communicate with an internal passage of the body to permit introduction and evacuation of sample material. The valve also includes a second pair of ports diametrically opposite the first pair of ports, the second pair of ports communicating between the internal passage and the exterior portion of said valve body. The valve also includes a rotor having an exterior surface movably engaging the interior passage of the valve. The rotor has a pair of opposed measured slots providing intermittent fluid communication between the respective first and second pairs of ports on the interior passage of the valve body. The slots retain a fixed volume of sample material while the slots are moved from alignment between one pair of ports and the opposite pair of ports. The valve also includes a tension-providing retainer engaging the rotor within the valve body.

The invention may define three separate temperature zones, the first temperature zone containing the first pair of ports upon the valve, the second temperature zone containing the second pair of ports on the valve, and the third temperature zone containing a chromatograph, wherein no change in temperature sufficient to condense any of a fixed volume of sample captured by the valve exists between said second and third temperature zones.

The present invention avoids the necessity of enclosing the valve body in an oven with the attendant complications of thermocouples and temperature measurement circuitry to control the heat. The present invention also avoids the need for heater collars which have been used historically to surround, the valve body to heat and vaporize the sample.

The present invention is an improvement over existing valves because the distance between the GC inlet and the port where a measured sample leaves the valve is minimized while at the same time the distance between that port and a port where sample material enters the valve is maximized.

The small distance between the GC inlet and the port where a measured sample leaves the valve, which minimizes dead volume, also minimizes the chances for a volatilized sample to condense. The large distance between the port where a measured sample leaves the valve and the port where sample material enters the valve minimizes the chances for pre-volatilization of sample material.

BRIEF DESCRIPTION OF THE DRAWINGS

FIG. 1 is a schematic view of a traditional Gas Chromatograph system;

FIG. 2 is a front view of a known sample valve, complete with heating collar, heater element, and transfer line;

FIG. 3 is an exploded perspective view of a valve according to one embodiment of the present invention;

FIG. 4 is a cross-sectional view of the valve body of FIG. 3;

FIG. 5 is a side perspective side view of the rotor of the valve body of FIG. 3;

FIG. 6 is a top perspective view of the rotor of the valve body of FIGS. 5;

FIG. 9 is another side perspective view of the valve body showing the carrier inlet line; and FIG. 10 is a side perspective view of the valve body of as seen from the opposite side of FIG. 9.

DETAILED DESCRIPTION OF THE INVENTION

Figure 7:
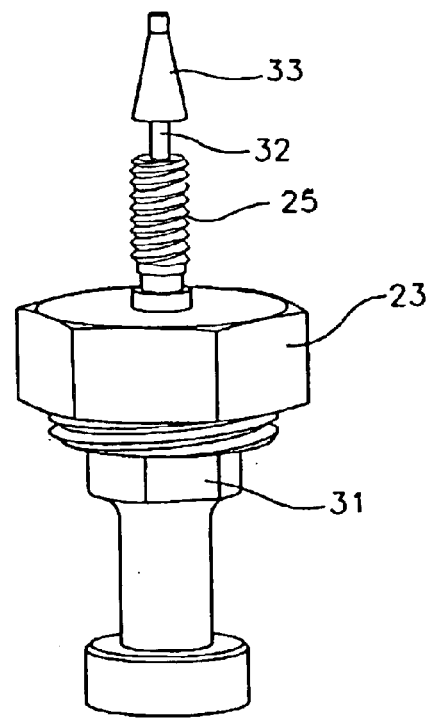
FIG. 7 is a front view of the sample inlet components of chromatograph.

The present invention relates to a new valve for a gas chromatograph (GC) which is mounted proximally adjacent the GC inlet. In prior art devices as shown in FIG. 2, the valve selectively moved a sample into the carrier gas stream for analysis through a port and tubing that was thermally isolated from the GC inlet. The present invention allows the valve to be placed in close proximity to the GC inlet (i.e. not thermally isolated). As a result the present invention provides temperature control of the sample within the valve and within the space between the valve and GC inlet.

Valve Body—General

FIG. 3 discloses the valve of the present invention. Valve body 10 is fashioned from stainless steel but can be formed by any non-reactive metal appropriate under the circumstances of its intended use. Valve body 10 may be machined from an integral stainless steel blank having a substantially round exterior portion 11 although the exterior portion 11 may be any shape including rectangular or hex-shaped. The valve body 10 provides an internal passage 1 there through providing an internal surface 13. The internal passage 1 may be tapered in a conical shape. Valve body 10 may further provide an extension 12 having threads 15 on its inner surface. A preload tensioning assembly 22 may be threaded into threads 15 on the valve body 10 to hold the rotor 20 in compressive engagement with the internal surface 13 of the passage 1 of the valve body 10.

Rotor

Rotor 20, as shown in FIG. 5, may formed from a stainless steel rod that provides a surface 21 which may be tapered and onto which is bonded a polymeric coating, in a manner well known to those skilled in this industry. The choice of the coating is dictated by the type of sample to be analyzed, and the pressure and temperature to which the sample is to be subjected. The coating on the rotor surface 21 sealingly engages the internal surface 13 of the valve body 10 so that the sample is confined to the slots 7 or 9. The slots 7 and 9 are shown as cylindrical troughs, but may have any shape.

Rotor 20 may also be fashioned on one end with a spline 18, shown in FIG. 6, that is used to engage the rotor with a stepper motor (not shown) that can be used to rotate the rotor 20 in the valve body 10. Rotor 20 can also be moved by other manual means in a manner well known to those in the GC industry without departing from the spirit of the present invention. FIG. 5 shows a relative spaced 180° relationship of the first slot 7 and the second slot 9 which are machined into the polymeric surface 21 of the rotor 20 to provide discrete and measured samples to the GC. Typical slot sizes may be varied from 0.06 $\mu$l up to 2 $\mu$l by exchanging the rotor 20 in a manner well known to those skilled in the GC industry. In the preferred embodiment, a 1 $\mu$l rotor 20 is used to sample most process streams efficiently. The slots 7 and 9 provide intermittent fluid communication between the first and second ports 2 and 4, or 6 and 8, on the internal passage 13 of the valve body shown in FIG. 4. As a slot 7 or 9 is aligned with a pair of ports 2 and 4, or 6 and 8, fluid flow is permitted from an inlet port to an outlet port. As the slot 7 or 9 is rotated out of alignment, flow is interrupted.

FIG. 6 is an end view of the rotor 20 showing the spline 18 used to engage the stepper motor internal spline to move the rotor 20 to load the sample into an injector body interface 25. In the improved invention the rotor 20 rotates in a single direction. Referring to FIGS. 3 and 4, the rotor 20 is preferably rotated in a direction such that a first slot 7 or 9 arrives at a sample inlet port 2 before a sample outlet port 4 and the opposite slot arrives at the carrier gas outlet port 6 before a carrier gas inlet port 8. The persistent direction of rotational movement limits wear on the surface 21 of the rotor 20 and the internal surface 13 of the valve body 10. In prior art devices, the movement of the rotor was in back and forth reversing directions to various ports around the periphery of the valve body causing wear and tear on the rotor surface. Since the slots 7 and 9 are opposed, excessive start and stop movement of the rotor 20 is eliminated. The rotor 20 is engaged and held in place by a tension-providing retainer 22 which may be threadedly engaged with the valve body 10.

Ports

FIG. 4 is a cross sectional view of the interior of the valve body 10 showing the spatial relationship of a sample inlet port 2, sample outlet port 4, carrier gas inlet port 8 and carrier gas outlet port 6. The valve body 10 may be threaded at the carrier gas inlet port 8 for connecting the inlet 27 of a carrier gas line 29. The ports 2 and 4 may be similarly threaded for attachment to a sampling supply and return line for intermittently, or continuously passing a sample through the adjacent slots 7 or 9. The ports provide communication from an exterior portion 11 of the valve body 10 to the internal passage 1. The sample ports 2 and 4 are diametrically opposed to the carrier gas ports 6 and 8. As a result, the length of the valve body 10 upon which a temperature gradient is produced is maximized. It follows that the temperature gradient, as described in more detail below can be maximized (i.e. the difference between highest and lowest temperature). This can be compared to other valves where the sample port and carrier gas port pairs are separated by approximately ninety degrees. In these valves the achievable range in the temperature gradient is dramatically reduced. As shown the ports in the present invention communicate between the internal passage 1 and a rounded cylindrical surface of the valve's exterior portion 11. The ports may also be configured to communicate between the internal passage 1 and a front or back surface of the exterior portion 11.

Figure 8:
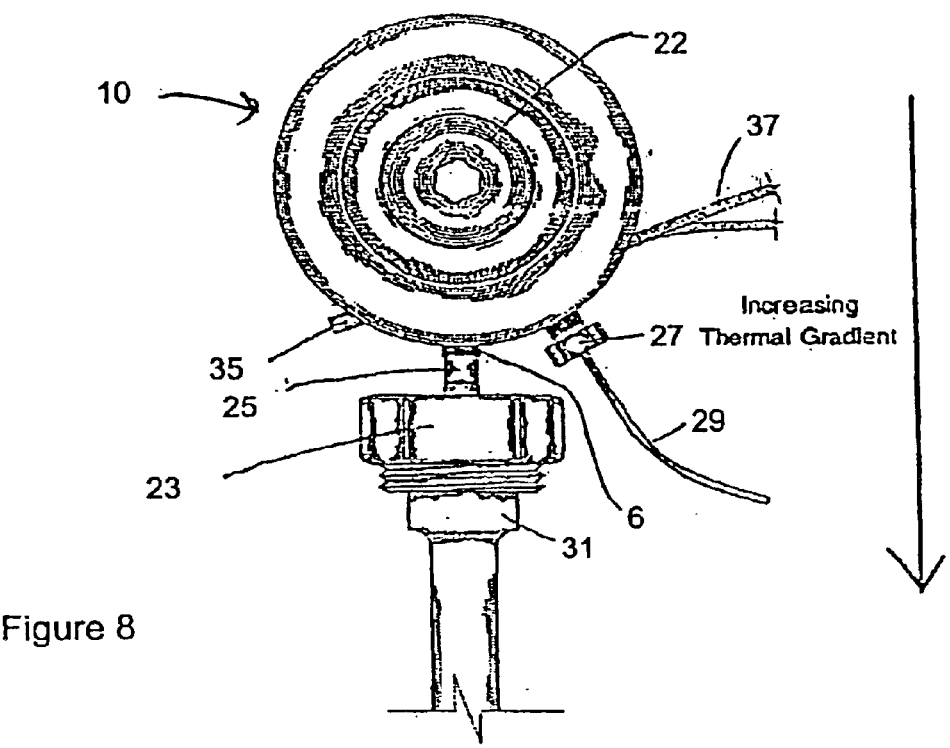
FIG. 8 is a front perspective view of the valve body showing the heater element, electric lead lines and the inlet line for carrier gas of the present invention.

As shown in FIG. 8, carrier gas outlet port 6 may be connected to the sample inlet portion of the chromatograph. The sample inlet portion may include a valve injector body interface 25 which is integrally connected to the septum cap 23 which is threaded on an injector body 31. A thin tube 32, seen in FIG. 7, carries the sample material from the valve body 10 to the chromatograph column. The tube includes a fitting 33 for attachment to the valve body 10. The orientation of the sample inlet portion components and thin tube 32 may be linear, permitting solely linear fluid communication from the interior passageway 1 of the valve body 10 to the column of the chromatograph. The thin tube 32 is short in comparison to known transfer lines and almost completely integral with the sample inlet portion components. This allows the sample material within the thin tube 32 to remain vaporized within the sample inlet portion components which are maintained at a suitable temperature.

Referring back to FIGS. 3 and 4, in use, the sample material (such as process liquids) flows into port 2 and out port 4, while carrier gas flows in port 8 and out port 6. To insert a measured sample into the GC column through the sample inlet portion, the rotor 20 is rotated in this preferred embodiment in a consistent direction of rotation to capture and move the sample material from the ports 2 and 4 flow path to the ports 6 and 8 flow path. The measured sample is volatilized as it moves into position and is immediately swept into the outlet port 6 by the carrier gas from inlet port 8. The sample is carried through the valve injector body interface 25, septum cap 23 and septum, and injector body 31 through the thin tube 32. In an alternate embodiment of the invention, the sample inlet portion does not include a septum and septum cap 23.

Temperature Gradient

Volatilization of the sample may be caused by heat applied to the portion of the valve body near the carrier gas outlet port 6. The heat is generated by the GC thermal generators (not shown) and in some situations additionally by a heating element 35 inserted in a passage 5. As may be readily appreciated, the location of the GC thermal generators (in the GC, heating the column and sample inlet portion) and in some cases heating element 35 on the bottom of the valve body, proximally adjacent the injector body interface 25 and carrier gas ports 6 and 8 permits a temperature gradient to be created in the valve body 10 between the sample inlet port 2 (colder) and the carrier gas outlet port 6 (hotter). A depiction of the temperature (thermal) gradient is shown in FIGS. 8–10.

Valve body 10 may be formed with a heater passage 5 that is drilled in a lower portion of the valve body 10 which can engage a standard heating element 35 (as shown in FIGS. 3 and 4) which is energized by conductors 37. FIG. 4 discloses the spaced relationship of the heater passage 5 which holds the heating element 35. The heater passage 5 and heating element 35 may be cylindrically shaped. The heater passage 5 and heating element 35 may be oriented generally perpendicular to an imaginary line bisecting a segment of the inner passage 1 between the first pair of ports 2 and 4 and extending through the center of the valve body 10. The heating element 35 may be shaped to extend a length which is shorter than the length of the heater passage 5 and centered within the passage 5 to concentrate closer along the centerline of the valve body 10. The heater element 35 may be programmed to turn on/off at desired times/temperatures.

In practice, by adjusting the amount of heat transferred to the valve at an end near the carrier gas outlet port 6 a preferred temperature gradient may be achieved. The heating element 35 is not a mandatory requirement. An embodiment of the invention uses solely heat transferred from the GC thermal generators, through the sample inlet portion, to heat the valve. The improvement allowing the valve to be placed closer to the GC allows a large amount of heat to be transferred from the hot GC itself over a short distance to the valve by simple conduction.

The present invention is an improvement over existing valves because the distance between a temperature zone around the GC and a temperature zone around the carrier gas outlet 6 of the valve body 10 is minimized while at the same time the distance between the carrier gas outlet temperature zone and a temperature zone around the sample inlet port 2 of the valve body 10 is maximized. The small distance between the GC temperature zone and the carrier gas outlet temperature zone minimizes the chances for a volatilized sample to condense (and minimizes dead volume). This distance may be as small as ⅜ inches. The large distance between the carrier gas outlet and sample inlet temperature zones minimizes the chances for pre-volatilization of sample material.

The present invention places the sample proximally at the point of injection upon full vaporization of the sample in the valve body 10. The distance between the carrier gas outlet port 6 (carrier gas outlet temperature zone) of the valve body 10 and the sample inlet (GC temperature zone) is approximately ⅜ inches as compared to the 1.5 to 2 inches in existing valves. By placing the sample inlet and outlet ports 2 and 4 diametrically opposite the carrier gas inlet and outlet ports 6 and 8, the distance between the sample inlet and carrier gas outlet temperature zones is maximized in any valve size.

Operation

The top portion of the valve body 10 adjacent the inlet port 2 may be maintained at ambient or near ambient temperature. This inhibits prevolatilization of the sample before it reaches the valve body 10. The movement of the sample from the sample ports 2 and 4 through the temperature gradient to the ports 6 and 8 adjacent the column inlet utilizes the temperature to volatilize the sample thereby providing an appropriately phased sample at the top of the chromatograph column. As the sample is moved to the port 6, the sample is volatilized and injected or swept into the injector body interface 25 by the carrier gas. The sample can be concentrated on the column by known temperature management techniques and introduced into the column by the continued flow of carrier gas or the temperature programming of the column, or both, at the direction of the chromatograph operator.

Sampling speed and uniformity are improved using the present invention. Speed is improved because as soon as a sample is discharged from a slot 7 through carrier gas outlet port 6, the opposite slot 9 is in position to receive sample material through sample inlet port 2. Also, the temperature gradient created within the rotor 21, which changes upon rotation of the rotor 21, may reach an equilibrium faster when a return rotational stroke of the rotor 21 is not required. Thus uniformity in the sampling process may be improved.

Results

As a result of utilizing the heat of the GC through the sample inlet portion of the chromatograph high molecular weight (high boiling point—in the range 1050F for $C_{44}$ hydrocarbons) materials can be analyzed by the improved valve body combination, avoiding condensation, and thereby obtaining clear, high definition chromatograms from the same sample throughout a wide molecular weight range. And the same invention, due to the diametric orientation of the sample ports and carrier gas ports allows for accurate analysis of gasoline, diesel fuels, crude oils, vacuum gas oils without any pre-volatilization.

It may be readily appreciated that the present invention can be used in any number of applications without departing from the spirit or intent of the invention. While a preferred form of the invention has been shown in the drawings and the specification, since variations in the preferred form will be apparent to those skilled in the art, the invention should not be construed as limited to the specific form shown and described.

What is claimed is:

1. A chromatograph valve for capturing sample material comprising:
    a valve body providing a first pair of ports formed through an exterior portion of said body, said first pair of ports communicating with an internal passage of said body to permit introduction and evacuation of sample material and further providing a second pair of ports opposite said first pair of ports, said second pair of ports communicating between said internal passage and said exterior portion of said valve body;
    a rotor having an exterior surface movably engaging said internal passage and having a pair of opposed measured slots providing intermittent fluid communication between the respective first and second pairs of ports on the internal passage of the valve body and retaining a fixed volume of sample material while the slots are moved from alignment between one pair of ports and the opposite pair of ports; a tension-providing retainer engaging the rotor within the valve body; and
    a member engaging one of said second pair of ports permitting solely linear fluid communication from said internal passageway of the valve body to a column on an adjacent chromatograph, wherein said member is a thin tube passing through an injector body interface, septum cap, septum and injector body.

2. The chromatograph valve of claim 1 wherein said first pair of ports are configured to receive a sample supply and return stream and said second pair of ports are configured to receive a carrier gas supply and return stream.

3. A chromatograph valve for capturing sample material comprising:
    a valve body providing a first pair of ports formed through an exterior portion of said body, said first pair of ports communicating with an internal passage of said body to permit introduction and evacuation of sample material and further providing a second pair of ports opposite said first pair of ports, said second pair of ports communicating between said internal passage and said exterior portion of said valve body;
    a rotor having an exterior surface movably engaging said internal passage and having a pair of opposed measured slots providing intermittent fluid communication between the respective first and second pairs of ports on the internal passage of the valve body and retaining a fixed volume of sample material while the slots are moved from alignment between one pair of ports and the opposite pair of ports;
    a tension-providing retainer engaging the rotor within the valve body;
    wherein said valve body includes a heater passage having a heating element engaged therein.

4. A method of capturing a volume of sample material to be tested in a gas chromatograph comprising the steps of:
    a. introducing a stream of sample material into a chromatograph valve, said valve comprising:
        a valve body providing a first pair of ports formed through an exterior portion of said body, said first pair of ports communicating with an internal passage of said body to permit introduction and evacuation of sample material and further providing a second pair of ports opposite said first pair of ports, said second pair of ports communicating between said internal passage and said exterior portion of said valve body;
        a rotor having an exterior surface movably engaging said internal passage and having a pair of opposed measured slots providing intermittent fluid communication between the respective first and second pairs of ports on the internal passage of the valve body and retaining a fixed volume of sample material while the slots are moved from alignment between one pair of ports and the opposite pair of ports; and
        a tension-providing retainer engaging the rotor within the valve body;
    b. introducing a carrier gas stream into said second pair of ports within said valve body;
    c. rotating said rotor and heating and at least partially volatilizing said fixed volume of sample using a heating element engaged within said valve body, capturing a sample volume within one of said slots and discharging said sample volume within said carrier gas through said second pair of ports.

5. A sampling system comprising:
    a gas chromatograph column being enclosed and temperature controlled; and
    a valve body providing a first temperature zone, at a first temperature, containing a first pair of ports formed through an exterior portion of said body, said first pair of ports communicating with an internal passage of said body to permit introduction and evacuation of sample material and further providing a second temperature zone, at a second temperature, containing a second pair of ports opposite said first pair of ports, said second pair of ports communicating between said internal passage and said exterior portion of said valve body;
    a rotor having an exterior surface movably engaging said internal passage and having a pair of opposed measured slots providing intermittent fluid communication between the respective first and second pairs of ports on the internal passage of the valve body and retaining a fixed volume of sample material while the slots are moved from alignment between one pair of ports and the opposite pair of ports;
    a tension-providing retainer engaging the rotor within the valve body; and
    a third temperature zone, at a third temperature, adjacent said second temperature zone and containing said chromatograph column;
    wherein said valve body is in fluid communication with said gas chromatograph column and wherein a sample introduced into said valve body is maintained in liquid form in the first temperature zone and in a vaporized form, at different temperatures from the first temperature zone, in the second and third temperature zones; and
    wherein said valve body further includes a heater passage having a heating element engaged therein.

6. A sampling system comprising:

a gas chromatograph column being enclosed and temperature controlled; and a valve body providing a first temperature zone containing a first pair of ports formed through an exterior portion of said body, said first pair of ports communicating with an internal passage of said body to permit introduction and evacuation of sample material and further providing a second temperature zone containing a second pair of ports opposite said first pair of ports, said second pair of ports communicating between said internal passage and said exterior portion of said valve body;

a rotor having an exterior surface movably engaging said internal passage and having a pair of opposed measured slots providing intermittent fluid communication between the respective first and second pairs of ports on the internal passage of the valve body and retaining a fixed volume of sample material while the slots are moved from alignment between one pair of ports and the opposite pair of ports;

a tension-providing retainer engaging the rotor within the valve body; and a third temperature zone adjacent said second temperature zone and containing said chromatograph column;

wherein said valve body is in fluid communication with said gas chromatograph column and wherein a sample introduced into said valve body is maintained in liquid form in the first temperature zone and in a vaporized form, at different temperatures from the first temperature zone, in the second and third temperature zones; and wherein said valve body further includes a thin tube passing through an injector body interface, septum cap, septum and injector body permitting solely linear fluid communication from said internal passageway of the valve body to a column on said chromatograph.

* * * * *